(12) United States Patent
Wong et al.

(10) Patent No.: US 8,084,581 B1
(45) Date of Patent: *Dec. 27, 2011

(54) METHOD FOR REMOVING UNMODIFIED HEMOGLOBIN FROM CROSS-LINKED HEMOGLOBIN SOLUTIONS INCLUDING POLYMERIC HEMOGLOBIN WITH A HIGH TEMPERATURE SHORT TIME HEAT TREATMENT APPARATUS

(76) Inventors: Bing Lou Wong, Irvine, CA (US); Sui Yi Kwok, Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 13/217,337

(22) Filed: Aug. 25, 2011

Related U.S. Application Data

(63) Continuation of application No. 13/097,183, filed on Apr. 29, 2011.

(51) Int. Cl.
*C07K 14/00* (2006.01)
*C07K 14/805* (2006.01)
*A61K 49/14* (2006.01)

(52) U.S. Cl. ....... 530/385; 514/1.1; 514/13.4; 514/13.5; 514/15.1

(58) Field of Classification Search .................. None
See application file for complete search history.

(56) References Cited

U.S. PATENT DOCUMENTS

| | | | |
|---|---|---|---|
| 3,925,344 A * | 12/1975 | Mazur ........................... | 530/385 |
| 4,001,401 A * | 1/1977 | Bonsen et al. ................ | 514/13.4 |
| 4,529,719 A | 7/1985 | Tye | |
| 4,543,209 A | 9/1985 | Tayot et al. | |
| 4,598,064 A | 7/1986 | Walder | |
| 4,600,531 A | 7/1986 | Walder | |
| 4,831,012 A | 5/1989 | Estep | |
| 4,987,048 A | 1/1991 | Shinozaki et al. | |
| 5,084,558 A | 1/1992 | Rausch et al. | |
| 5,189,146 A | 2/1993 | Hsia | |
| RE34,271 E | 6/1993 | Walder | |
| 5,250,665 A | 10/1993 | Kluger et al. | |
| 5,296,465 A | 3/1994 | Rausch et al. | |
| 5,344,393 A | 9/1994 | Roth et al. | |
| 5,439,882 A | 8/1995 | Feola et al. | |
| 5,451,205 A | 9/1995 | Roth et al. | |
| 5,464,814 A | 11/1995 | Sehgal et al. | |
| 5,591,710 A | 1/1997 | Hsia | |
| 5,618,919 A | 4/1997 | Rausch et al. | |
| 5,631,219 A | 5/1997 | Rosenthal et al. | |
| 5,691,453 A | 11/1997 | Wertz et al. | |
| 5,725,839 A | 3/1998 | Hsia | |
| 5,741,893 A | 4/1998 | Hsia | |
| 5,741,894 A | 4/1998 | Azari et al. | |
| 5,753,616 A | 5/1998 | Rausch et al. | |
| 5,767,089 A | 6/1998 | Hsia | |
| 5,789,376 A | 8/1998 | Hsia | |
| 5,804,561 A | 9/1998 | Hsia | |
| 5,807,831 A | 9/1998 | Hsia | |
| 5,811,005 A | 9/1998 | Hsia | |
| 5,814,601 A | 9/1998 | Winslow et al. | |
| 5,817,528 A | 10/1998 | Bohm et al. | |
| 5,817,632 A | 10/1998 | Hsia | |
| 5,824,781 A | 10/1998 | Hsia | |
| 5,840,701 A | 11/1998 | Hsia | |
| 5,840,851 A | 11/1998 | Plomer et al. | |
| 5,865,784 A | 2/1999 | Faithfull et al. | |
| 5,895,810 A | 4/1999 | Light et al. | |
| 5,905,141 A | 5/1999 | Rausch et al. | |
| 5,955,581 A | 9/1999 | Rausch et al. | |
| 6,007,774 A | 12/1999 | Faithfull et al. | |
| 6,054,427 A | 4/2000 | Winslow | |
| 6,127,043 A | 10/2000 | Lange | |
| 6,160,098 A | 12/2000 | Kerwin | |
| 6,242,417 B1 | 6/2001 | Gerber et al. | |
| 6,270,952 B1 | 8/2001 | Cook et al. | |
| 6,288,027 B1 | 9/2001 | Gawryl et al. | |
| 6,323,175 B1 | 11/2001 | Hsia | |
| 6,399,357 B1 | 6/2002 | Winge | |
| 6,432,918 B1 | 8/2002 | Winslow | |
| 6,486,306 B1 | 11/2002 | Winge | |
| 6,506,725 B1 | 1/2003 | Rausch et al. | |
| RE38,081 E | 4/2003 | Faithfull et al. | |
| 6,566,504 B2 | 5/2003 | Bhattacharya et al. | |
| 6,599,878 B2 | 7/2003 | Rooney | |
| 6,610,832 B1 | 8/2003 | Gawryl et al. | |
| 6,709,810 B2 | 3/2004 | Cook et al. | |
| 6,740,139 B2 | 5/2004 | Russell et al. | |

(Continued)

FOREIGN PATENT DOCUMENTS

WO     WO 89/12456     12/1989

OTHER PUBLICATIONS

Napolitano LM., "Hemoglobin-based oxygen carriers: first, second or third generation? Human or bovine? Where are we now?", Crit Care Clin. 25, 279-301 (2009).

Jiin-Yu Chen et al., "A review of blood substitutes: examining the history, clinical trial results, and ethics of hemoglobin-based oxygen carriers", Clinics 64(8), 803-813 (2009).

Larny ML et al., "Randomized Trial of Dlaspirin Cross-linked Hemoglobin Solution as an Alternative to Blood Transfusion after Cardiac Surgery", Anesthesiology 92(3), 646-656 (2000).

Lois R. Manning et al., "Subunit dissociations in natural and recombinant hemoglobins", Protein Science 5(4), 775-781 (1996).

Ronald Kluger et al., "Protein-protein coupling and its application to functional red cell substitutes", Chom Commun (Camb). 46(8), 1194-1202 (2010).

Ronald Kluger, "Red cell substitutes from hemoglobin—do we start all over again?", Current Opinion in Chemical Biology 14(4), 538-543 (2010).

(Continued)

*Primary Examiner* — Anand Desai
(74) *Attorney, Agent, or Firm* — Ella Cheong Hong Kong; Margaret Burke; Sam Yip

(57) ABSTRACT

A method heat treatment of cross-linked hemoglobin solutions including polymeric hemoglobin is disclosed. The method involves contacting the hemoglobin solution with a high temperature short time heat treatment apparatus. The high temperature short time process thermally denatures unmodified tetrameric hemoglobin (hemoglobin dimer form), protein impurities (e.g. immunoglobin-G, serum albumin), bacteria, and viruses so that renal injury, vascular detrimental effects and other toxicity reactions can be avoided.

10 Claims, 3 Drawing Sheets

U.S. PATENT DOCUMENTS

| | | |
|---|---|---|
| 6,747,132 B2 | 6/2004 | Privalle et al. |
| 6,844,317 B2 | 1/2005 | Winslow et al. |
| 6,894,150 B1 | 5/2005 | Tye |
| 7,038,016 B2 | 5/2006 | Talarico et al. |
| 7,101,846 B2 | 9/2006 | Winslow |
| 7,293,985 B2 | 11/2007 | Cook et al. |
| 7,411,044 B2 | 8/2008 | Avella et al. |
| 7,435,795 B2 | 10/2008 | McGinnis et al. |
| 7,494,974 B2 | 2/2009 | Tye |
| 7,501,499 B2 | 3/2009 | Acharya et al. |
| 7,504,377 B2 | 3/2009 | Tye |
| 7,553,613 B2 | 6/2009 | Gawryl et al. |
| 7,625,862 B2 | 12/2009 | Winslow et al. |
| 7,655,392 B2 | 2/2010 | Stassinopoulos |
| 7,759,306 B2 | 7/2010 | Simoni et al. |
| 7,795,401 B2 | 9/2010 | Huang et al. |
| 7,932,356 B1 | 4/2011 | Wong et al. |
| 7,989,593 B1 | 8/2011 | Wong et al. |
| 2007/0142626 A1 | 6/2007 | Kluger et al. |

OTHER PUBLICATIONS

Kenji Sampel et al., "Role of nitro oxide scavenging in vascular response to cell-free hemoglobin transfusion", Am J Physiol Heart Ciro Physiol 289(3), H1191-H1201 (2005).

Tao Hu et al., "Preparation and characterization of dimeric bovine hemoglobin tetramers", Journal of Protein Chemistry 22(5), 411-416(2003).

Tao Hu et al., "PEGylation of Val-1(alpha) destabillizes the tetrameric structure of hemoglobin", Biochemistry 48(3), 608-616 (2009).

Kim D Vandegriff et al., "Hemospan: design principles for a new class of oxygen therapeutic", Artificial organs 33(2), 133-138 (2009).

Thoralf Komer et al., "DCL-Hb for trauma patients with severe hemorrhaglo shock: the European "On-Scene " multicenter study", Intensive Care Medicine 29(3), 378-385 (2003).

Chad R. Hansey et al., "Purification and chemical modifications of hemoglobin in developing hemoglobin based oxygen carriers", Advanced Drug Delivery Reviews 40(3), 153-169 (2000).

Donat R. Spahn et al., "Artificial O2 carriers: Status in 2005", Current pharmaceutical design 11(31), 4099-4114 (2005).

Andre F. Palmer et al., "Tangential flow filtration of hemoglobin", Biotechnol Prog. 25(1), 189-199 (2009).

David C. Irwin et al., "Polymerized bovine hemoglobin decreases oxygen during normoxia and acute hypoxia in the rat", Am J Physiol Hoarl Circ Physiol 295(3), H1090-H1099 (2008).

Guoyong Sun et al, "Preparation of Ultrapure Bovine and Human Hemoglobin by Anlon Exchange Chromatography", J Chromatogr B Analyt Technol Biomed Life Sci. 867(1), 1-7 (2008).

Yiping Jia et al., "Effects of cross-linking and zero-link polymerization on oxygen transport and redox chemistry of bovine hemoglobin", Biochimica et Biopyhysica Acta 1794(8), 1234-1242 (2009).

Cai Jin et al., "Chemically Modified Porcine Hemoglobins and Their Biological Properties", Proteins and Peptide Letters, vol. 11, No. 4, 353-360 (2004).

Malavalli, J. of Protein Chemistry, vol. 19, No. 4, 2000, pp. 255-267.

Hu, Biochem. J. vol. 402, 2007, pp. 143-151.

Jones, J. of Biological Chemistry, vol. 271, No. 2, 1996, pp. 675-680.

Chatterjee, J. of Biological Chemistry, vol. 261, No. 21, 1986, pp. 9929-9937.

Ji, Proteins: Structure, Function, and Genetics, vol. 30, 1998, pp. 309-320.

Kavanaugh, Biochemistry, vol. 27, 1988, pp. 1804-1808.

Kwansa, Proteins; Structure, Function, and Genetics, vol. 39, 2000, pp. 166-169.

Manning, Proc. Nat'l. Acad. Sci. USA, vol. 88, 1991, pp. 3329-3333.

Snyder, Proc. Nat'l. Acad. Sci. USA, vol. 84, 1987, pp. 7280-7284.

* cited by examiner

METHOD FOR REMOVING UNMODIFIED HEMOGLOBIN FROM CROSS-LINKED HEMOGLOBIN SOLUTIONS INCLUDING POLYMERIC HEMOGLOBIN WITH A HIGH TEMPERATURE SHORT TIME HEAT TREATMENT APPARATUS

FIELD OF THE INVENTION

The invention relates to the field of hemoglobin-based oxygen carriers and, more particularly, to heat treatment techniques for purifying hemoglobin-based oxygen carriers including polymeric hemoglobin.

BACKGROUND OF THE INVENTION

There exists a need for a blood-substitute to treat or prevent hypoxia resulting from blood loss (e.g., from acute hemorrhage or during surgical operations), resulting from anemia (e.g., pernicious anemia or sickle cell anemia) or resulting from shock (e.g., volume deficiency shock, anaphylactic shock, septic shock or allergic shock).

The use of blood and blood fractions as in this capacity as a blood-substitute is fraught with disadvantages. For example, the use of whole blood often is accompanied by the risk of transmission of hepatitis-producing viruses and AIDS-producing viruses which can complicate patient recovery or result in patient fatalities. Additionally, the use of whole blood requires blood-typing and cross-matching to avoid immunohematological problems and inter donor incompatibility.

Hemoglobin, as a blood-substitute, possesses osmotic activity and the ability to transport and transfer oxygen. However, aqueous hemoglobin exists in equilibrium between the tetrameric (65 KDa) and dimeric (32 KDa) forms. Hemoglobin dimers are excreted by the kidney and result in rapid intravascular elimination of hemoglobin solutions with such solutions typically having a 2-4 hour plasma half-life.

Efforts have been directed to overcome the inherent limitations of hemoglobin solutions by molecularly modifying the hemoglobin. Intramolecularly and intermolecularly cross-linking hemoglobin has generally reduced renal elimination and increased intravascular retention time.

However, solutions of cross-linked hemoglobin still typically contain a significant fraction of unmodified tetrameric hemoglobin. This unmodified tetrameric hemoglobin can convert to dimeric hemoglobin and then be excreted from the body, thereby reducing the average intravascular retention time for cross-linked hemoglobin blood-substitutes. Furthermore, current means for separation, such as standard filtration, do not adequately distinguish between unmodified tetrameric hemoglobin and modified tetrameric hemoglobin.

Thus, in spite of the recent advances in the preparation of cross-linked hemoglobin blood-substitutes, the need continues to exist for a method to effectively separate unmodified hemoglobin from a solution of an intramolecularly and/or intermolecularly cross-linked hemoglobin blood-substitute to improve the average intravascular retention time of the blood-substitute and to prevent significant levels of renal excretion of hemoglobin.

Prior approaches to removal of various impurities from hemoglobin solutions has focused on relatively low temperature long term (longer than one hour) heat treatment processes. U.S. Pat. No. 5,281,579 describes heat treatment from 45 to 85° C., and particularly 60-66° C. for 1 to 30 hours. U.S. Pat. No. 5,741,894 describes a process for removal of impurities from partially oxygenated hemoglobin solutions in a range of 45 to 85° C., and particularly 76° C. for 90 minutes. However, such long term heat treatment conditions can lead to the formation of met-hemoglobin, which cannot be used to oxygenate tissues. Further, such long term heat treatment processes are not compatible with commercial-scale production processes.

SUMMARY OF THE INVENTION

The present invention relates to a method for separating unmodified hemoglobin from cross-linked hemoglobin in a hemoglobin solution including polymeric hemoglobin. The method involves contacting the hemoglobin solution with a high temperature short time apparatus wherein unmodified tetrameric hemoglobin is thermally denatured to form a precipitate. The denatured and precipitated hemoglobin dimers are then separated from the solution, while retaining the cross-linked hemoglobin in the solution.

The advantages of this invention include providing a blood-substitute with an improved intravascular retention time, a reduction or elimination of significant renal elimination of hemoglobin and the side effects associated therewith, a suitable oncotic pressure, and reduced hypertensive effects.

DETAILED DESCRIPTION OF THE INVENTION

Figure 1:
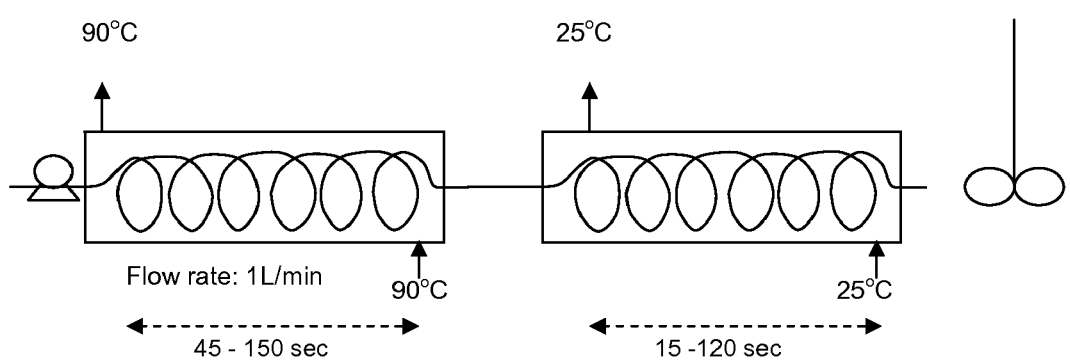
FIG. 1 represents a schematic flow diagram of a high temperature short time apparatus method for denaturing unmodified hemoglobin from modified hemoglobin blood-substitute according to the present invention.

Hemoglobin (Hb) suitable for Hb solutions of this invention can be derived from new, old or outdated blood from humans and other vertebrates, such as cattle, pigs, sheep, ducks and chickens.

The blood can be collected from live or freshly slaughtered donors. Examples of suitable methods for obtaining hemoglobin, derived from red blood cells, are described in U.S. Pat. Nos. 5,084,558 and 5,296,465, issued to Rausch et al, U.S. Pat. No. 6,498,141, issued to DeWoskin et al, and U.S. Pat. No. 7,291,592, issued to Gould et al. The teachings of U.S. Pat. Nos. 5,084,558, 5,296,465, 6,498,141 and 7,291,592 are incorporated herein by reference in their entirety.

In a preferred embodiment, hemoglobin is derived from red blood cells as described in U.S. Pat. No. 5,955,581, the teachings of which are incorporated herein by reference in their entirety.

Suitable hemoglobin solutions comprise aqueous solutions of dissolved Hb wherein the dissolved Hb includes unmodified Hb in addition to modified tetrameric Hb and/or polymeric Hb.

Unmodified hemoglobin, as defined herein, is hemoglobin in a non-dissociated and uncross-linked tetrameric form which can dissociate into Hb dimers in vitro or in vivo; unmodified hemoglobin may also include dissociated Hb dimers. Hb dimers can further dissociate into Hb subunits (monomers). Modified hemoglobin may be intramolecularly cross-linked into stable tetramers as well as intermolecularly cross-linked into a polymer chain within the Hb solution. A polymer-containing hemoglobin solution used as the starting solution of the present invention can include cross-linked tetrameric hemoglobin along with intermolecularly cross-linked polymeric hemoglobin, and also include undesirable unmodified hemoglobin in tetrameric or dimeric form.

Polymeric hemoglobin may include only hemoglobin components as set forth in U.S. Pat. Nos. 5,753,616, 5,895,810 and 6,288,027, the disclosures of which are incorporated by reference herein; it may include non-hemoglobin molecules conjugated with hemoglobin such as polyethylene glycol (PEG). Such materials are described in U.S. Pat. Nos. 7,169,900, 7,501,499, and 7,795,401, the disclosures of which are incorporated by reference herein. All of the above materials can be used as starting hemoglobin-containing solutions in the dimer-removal processes described below. Commercially available hemoglobin-based oxygen carriers can also be used in the dimer-removal process of the present invention, including HEMOPURE®, OXYGLOBIN®, POLYHEME®, HEMOLINK™ and MP4.

In the process of the present invention, a polymeric hemoglobin-containing solution prepared according to any of the above teachings is subjected to a heat treatment process from approximately 80° C. to approximately 95° C., and, more preferably, greater than 85° C. to 95° C. to successfully remove uncross-linked tetrameric and dimeric forms of hemoglobin from the polymeric hemoglobin-containing solution. Any precipitates formed during the heat treatment are removed by centrifugation or a filtration apparatus to form a clear hemoglobin-containing solution. The high temperature short time heat treatment is preferably carried out using the apparatus depicted in FIG. 1 and described in more detail in Example 1. In this temperature range, all of the heat treatments can take place for durations of substantially less than one hour. In the lower range of 80-85° C., a time of about 20 to 40 minutes is sufficient. In a temperature range of greater than 85° C. and less than 90° C. a period from 8 to about 30 minutes is sufficient. However at higher temperatures, such as 90-95° C., the heat treatment can be performed in an exemplary embodiment in 5 minutes or less, and more preferably in less than three minutes. Cooling preferably takes less than two minutes, and more preferably less than one minute to minimize formation of met-hemoglobin.

The high temperature short time process for heat treating the hemoglobin solutions in the purification process also removes other impurities, for example immunoglobin-G and harmful microbial materials and viruses, so that renal injury, vascular detrimental effects and other toxicity reactions can be avoided.

Heat treatment of tetrameric hemoglobin is described in U.S. Pat. No. 7,932,356 and U.S. patent application Ser. Nos. 12/821,214 and 13/013,850 all of the disclosures of which are incorporated herein by reference. The heat treated polymeric hemoglobin of the present invention can be packaged as described in U.S. Pat. No. 7,932,356 and can be used in various tissue oxygenation techniques disclosed in the above patents and applications. The highly purified and heat stable oxygen carrier-containing pharmaceutical composition is used in methods of oxygenating tissue in which the composition is provided to animal tissue either in vivo or ex vivo as described in the '356 patent.

EXAMPLE 1

HTST Heat Processing

A High Temperature Short Time (HTST) processing apparatus is shown in FIG. 1. A heating process using the HTST processing apparatus is performed on the polymeric hemoglobin-containing starting material. In this example, the condition for heat treatment is 90° C. for 30 seconds to 3 minutes, and preferably 45 to 60 seconds; although other conditions can be selected as discussed above and the apparatus modified accordingly. A solution containing polymeric hemoglobin, that is commercially available Oxyglobin®, is optionally treated with 0.2% of N-acetyl cysteine and pumped into a HTST processing apparatus (first section of the HTST heat exchanger is pre-heated and maintained at 90° C.) at a flow rate of 1.0 liter per minute, the residence time of the first section of the apparatus is between 45 to 60 seconds, then the solution is passed through at the same flow rate into another section of the heat exchanger that is maintained at 25° C. The time required for cooling is between 15 to 30 seconds. After cooling down to approximately 25° C., N-acetyl cysteine is optionally added immediately afterward at a concentration of 0.2% to 0.4%, preferably at 0.4%. This chemical addition after the HTST heating process maintains met-hemoglobin (inactive hemoglobin) at a low level. The set-up of the processing apparatus is easily controlled for industrial operation. If the hemoglobin is not cross-linked, it is not heat stable and forms a precipitate after the heat treatment step. The precipitate is then removed by a centrifugation or a filtration apparatus to form a substantially clear solution thereafter.

Figure 2:
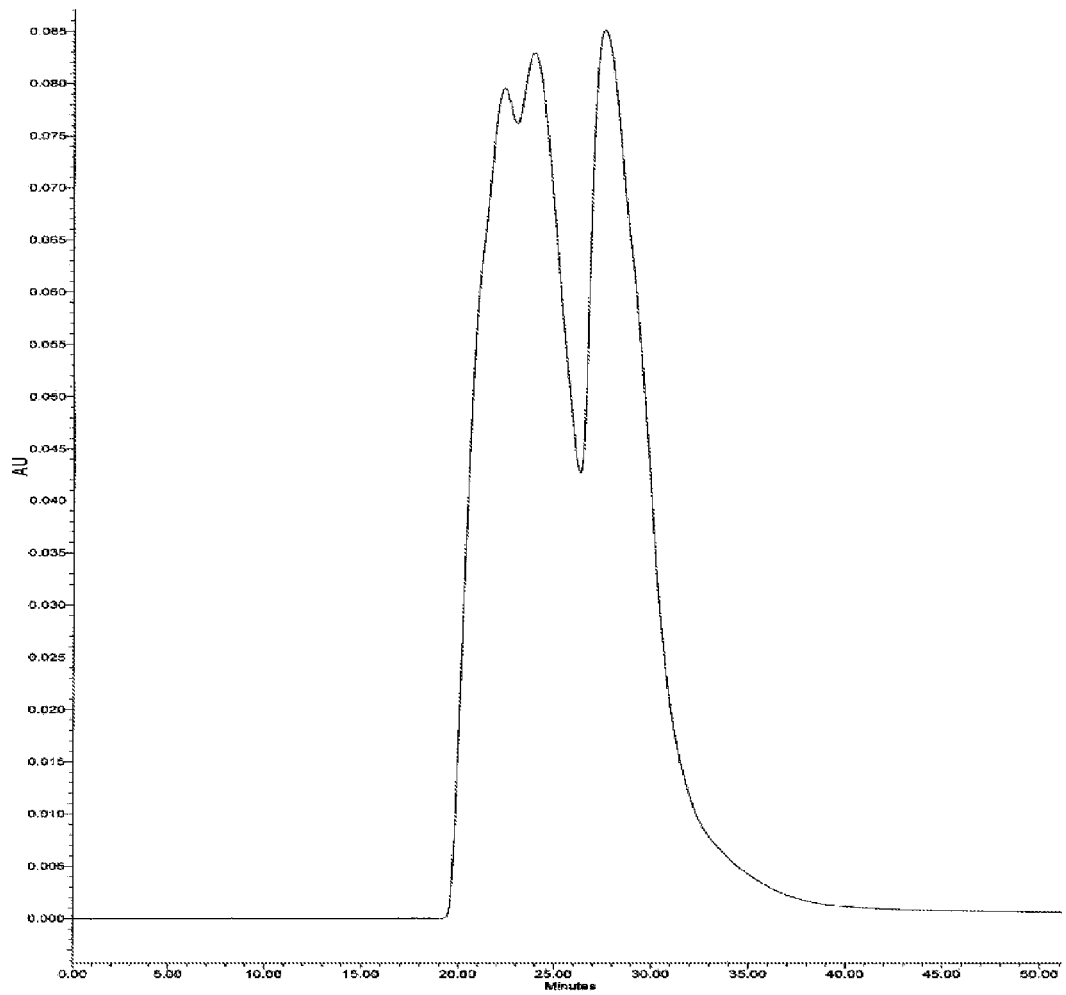
FIG. 2 depicts high performance liquid chromatography analysis for non-heat treated polymeric hemoglobin.
Figure 3:
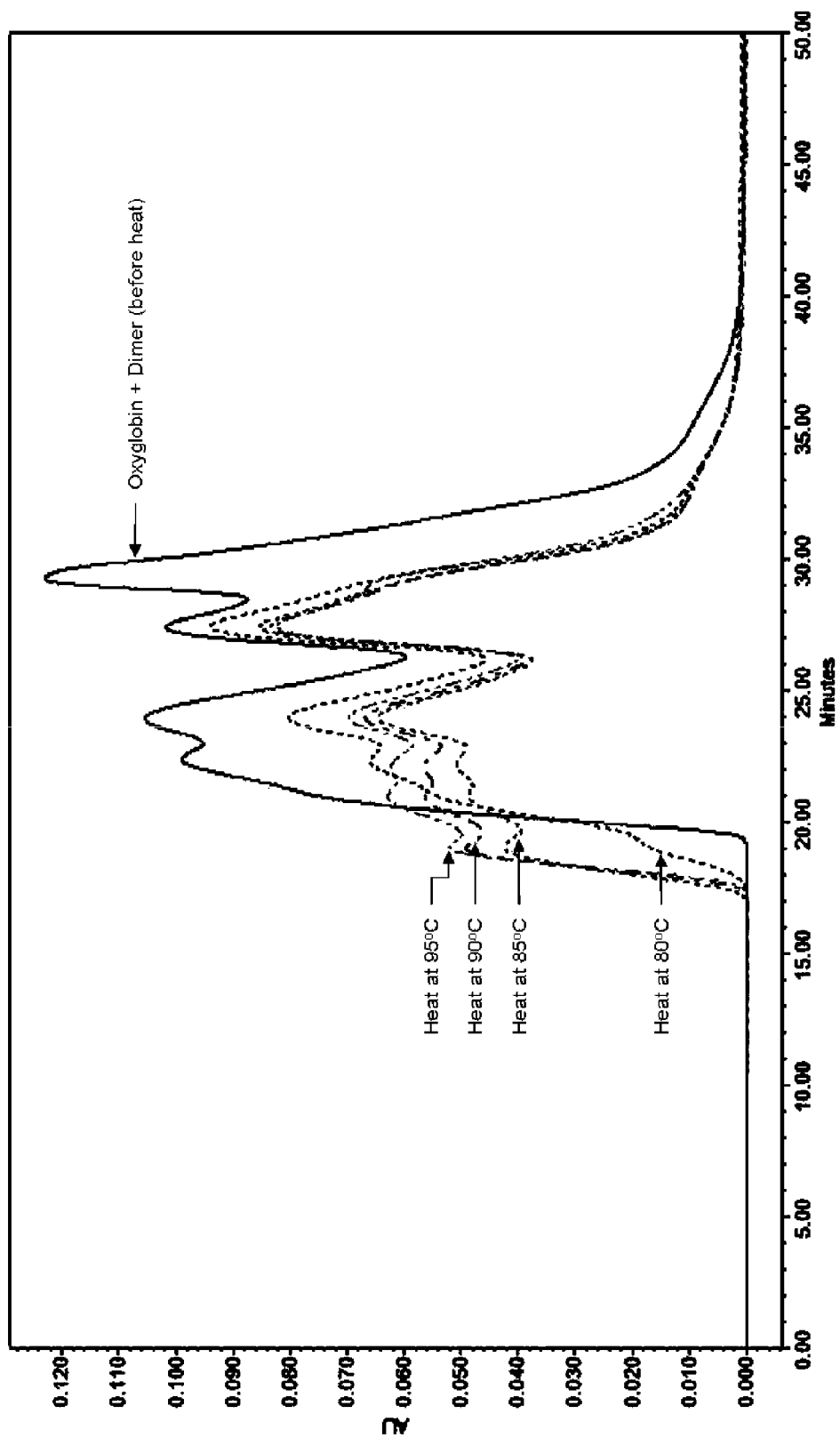
FIG. 3 depicts high performance liquid chromatography analysis for (a) non-heat treated polymeric hemoglobin with spiked hemoglobin dimer and (b) heat stable polymeric hemoglobin in which has undergone short term heat treatment at 80° C., 85° C., 90° C. and 95° C. respectively.

FIG. 2 shows the molecular weight distribution of polymeric hemoglobin by size-exclusion High Performance Liquid Chromatography (HPLC). The molecular weight distribution for polymeric hemoglobin solution ranges from 32 KDa to >500 KDa. Following the HTST heat process step (from 80° C. to 95° C.) in our invention, the spiked dimeric form of hemoglobin can be removed successfully from the polymeric hemoglobin solution (shown in FIG. 3). Any precipitates formed during the HTST heat process step are removed by centrifugation or a filtration apparatus to form a substantially clear cross-linked hemoglobin solution.

Hemox Analyzer for p50 (oxygen partial pressure, at which the hemoglobin solution is 50% saturated) measurement is used thereafter to analyze the (a) non-heat treated polymeric hemoglobin-containing solution, and (b) a heat treated polymeric hemoglobin-containing solution (undergo 80° C. treatment). No significant change in hemoglobin content (as measured by Co-Oximetry) is detected between (1) before HTST heat process step, and (2) after HTST heat process step. However, the p50 value is shifted to a lower value (from 37.5 mmHg to 23.3 Hg) after HTST heat process step. This indicates that the hemoglobin-oxygen binding affinity is higher. The lowering of p50 value is an advantage to upload oxygen in hypoxic tissues and hypoxic tumor cells. As a tumor grows, it rapidly outgrows its blood supply, leaving portions of the tumor with regions where the oxygen concentration is significantly lower than in healthy tissues. Denny (Denny W. A., Prodrug strategies in cancer therapy, Eur. J. Med. Chem., 2001, 36, 577-595) reported that hypoxic tumor cells are usually resistant to radiotherapy and chemotherapy; however, they can be made more susceptible to treatment by increasing their oxygen content.

TABLE 1

| | p50 value (mmHg) |
|---|---|
| Non-heat treated polymeric hemoglobin-containing solution | 37.5 |
| Heat treated polymeric hemoglobin-containing solution | 23.3 |

EXAMPLE 2

Oxyglobin® and/or Hemopure® Polymeric Hemoglobin

Synthesis of Stable Polymeric Hemoglobin Blood-Substitute based on the description of U.S. Pat. Nos. 5,895,810, 5,296,465, 5,084,558, 5,753,616 and 5,955,581, is also known as Oxyglobin® and/or Hemopure® product, the disclosures of which are incorporated by reference herein.

The following example relates to a method for making polymeric-containing hemoglobin solutions which are suitable for treatment by the heat treatment apparatus and method of the present invention.

Bovine whole blood is collected, mixed with a sodium citrate anticoagulant to form a blood solution. The red blood cells (RBCs) are isolated from bovine whole blood. The RBCs are then washed to separate extracellular plasma proteins, such as BSA or IgG, from the RBCs. Following separation of the RBCs, the RBCs are lysed to form a hemoglobin-containing solution.

The concentrated Hb solution is then directed from the ultrafiltrate tank onto the media contained in parallel chromatographic columns to separate the Hb by high performance liquid chromatography. The chromatographic columns contain an anion exchange medium suitable to separate Hb from nonhemoglobin proteins. The anion exchange media is a quaternary ammonium anion exchange medium on silica gel. This method of treating silica gel is described in the Journal of Chromatography, 120:321-333 (1976).

The Hb solution is then deoxygenated to a level where oxyhemoglobin or $HbO_2$ content is about 101. During deoxygenation, temperature of the Hb solution is maintained between about 19° C. and about 31° C. Also during deoxygenation, and subsequently throughout the process, the Hb is maintained in a low oxygen environment to minimize oxygen absorption by the Hb and to maintain an oxygenated Hb ($HbO_2$) content of less than about 10% in the deoxy-Hb.

Prior to the polymerization process, depyrogenated and oxygen-depleted "water for injection" (WFI) is added to the Hb solution to a concentration of about 40 g Hb/L. The polymerization is conducted in a 12 mM phosphate buffer with a pH of 7.8, having a chloride concentration less than or equal to about 35 mM.

The oxidation-stabilized deoxy-Hb and N-acetyl cysteine (NAC) are subsequently slowly mixed with the cross-linking agent glutaraldehyde, specifically 29.4 grams of glutaraldehyde for each kilogram of Hb over a five hour period, while heating at 42° C. and recirculating the Hb solution through a Kenics 1½ inch static mixer with 6 elements (Chemineer, Inc.), to form a polymeric Hb solution (hereinafter "poly(Hb)"). After polymerization, the temperature of the poly(Hb) in the polymerization reactor is reduced to a temperature between about 18° C. to about 22° C.

The poly(Hb) is then concentrated by recirculating the poly(Hb) through the ultrafilter until the concentration of the poly(Hb) is increased to about 85 g/L. A suitable ultrafilter is a 30 KDa ultra filter. Subsequently, the poly(Hb) solution is then mixed with 66.75 g sodium borohydride, and then recirculated through the static mixer at a flow rate of 10-20 liters per minute.

After the pH and electrolytes are restored to physiologic levels, the stable polymeric Hb blood-substitute is then diluted to a concentration of 50 g/L by adding the filtered, deoxygenated low pH buffer to the polymerization reactor. The diluted blood-substitute is then diafiltered by recirculating from the polymerization reactor through the static mixer and a 100 KDa purification filter against a filtered deoxygenated buffer containing 27 mM sodium lactate, 12 mM NAC, 115 mM NaCl, 4 mM KCl and 1.36 mM $CaCl_2$ in WFI, (pH 7.8). Diafiltration continues until the blood-substitute contains less than or equal to about 10% modified tetrameric and unmodified tetrameric species.

A polymeric Hb solution is formed according to the method described in this Example 2 (according to the description of U.S. Pat. No. 5,084,558, issued to Rausch et al.). This Hb solution is analyzed by gel permeation chromatography and found to comprise about 45% Hb dimers, about 15% unmodified Hb tetramers, and about 40% polymeric Hb molecules which are larger than unmodified tetramers.

The polymeric hemoglobin-containing material may then be subjected to the heat treatment as discussed in Example 1 to remove dimer and unmodified Hb tetramer.

EXAMPLE 3

Polyheme® Polymeric Hemoglobin

Synthesis of Stable Polymeric Hemoglobin Blood-Substitute based on the description of U.S. Pat. Nos. 6,498,141 and 7,291,592, is also known as Northfield laboratories Inc. product (Polyheme®), the disclosures of which are incorporated by reference herein.

The following example relates to a method for making polymeric-containing hemoglobin solutions suitable for treatment by the heat treatment apparatus and method of the present invention.

(3a) Preparation of Red Blood Cells, Cell Wash and Lysis

Mix a blood solution with a 1% aqueous sodium chloride solution to form a 4% total hemoglobin solution; carbon monoxide is then introduced into the mixing tank so that the tank contains an atmosphere of carbon monoxide.

By coupling to a 0.65 μm tangential flow filter, this 4% total hemoglobin solution is washed with about 8 volumes of the 1% sodium chloride solution to remove plasma protein contaminants. Subsequent to washing, the solution is concentrated to about 16% total hemoglobin, and "water for injection" (WFI) is added to bring the volume of the solution up to about 2.5 times volume. With the addition of the WFI, the cells swell and rupture releasing hemoglobin into solution. The concentration of the resulting hemoglobin solution is about 7% total hemoglobin.

The resulting solution is clarified; red blood cells stroma contaminants and cell wall material is retained and removed by the filter. The remaining solution is about 3.3% total hemoglobin solution.

(3b) Heat Treatment, Clarification and Viral Reduction

The resulting solution of stroma-free hemoglobin is then heat treated at a temperature of about 60-62° C. over a period of about 10 hours. During this time, the solution is moderately agitated. As the solution is heated and passes a temperature of about 55° C., a precipitate forms.

The resulting 3.3% total hemoglobin (w/v) stroma-free, heat treated hemoglobin solution is then filtered through a 0.2 μm pre-filter followed by a 0.1 μm pre-filter and then pumped through a 100 KDa viral reduction ultra filter.

(3c) Ultra-Filtration Concentration

The filtered hemoglobin solution is then concentrated to about 14% total Hb concentration and subsequently washed and diafilter with 4 volumes of WFI. The concentration and diafiltration is accomplished using a 10 KDa ultra filter. This hemoglobin in the solution is primarily carboxyhemoglobin.

(3d) Gas Exchange with Oxygen and Nitrogen

The resulting carboxyhemoglobin solution is sparged with a flow of oxygen for 18 hours at 10° C. The resulting solution contains less than 5% carboxyhemoglobin based on the weight of total hemoglobin.

After oxygenation, the solution is sparged with a similar flow of nitrogen for about 3 to 3.5 hours at 10° C. until less than 10% oxyhemoglobin based on the weight of total hemoglobin remains in the solution.

(3e) Chemical Modification

The deoxyhemoglobin (at about 4° C.) solution is then added an aqueous solution of pyridoxyl-5-phosphate (P5P) (93.75 g/L) at a 2:1 P5P to hemoglobin molar ratio. The pyridoxylation is conducted at a temperature of about 4° C. The P5P solution is typically added over about 1 minute and mixed for approximately 15 minutes, after which a sodium borohydride/sodium hydroxide solution is added to the hemoglobin solution at a ratio of 0.8 g of sodium hydroxide and 90.8 g of sodium borohydride per 2 liters of hemoglobin solution. The borohydride solution is added as rapidly as possible over a period of about 1 minute and then stirred for one hour. The resulting solution of pyridoxylated hemoglobin is subsequently diafiltered using 10 KDa ultra filter to remove excess reactants with 4 volumes of WFI.

(3f) Polymeric Hemoglobin Solution

The pyridoxylated hemoglobin is added sufficient WFI to prepare a 4.5% total hemoglobin solution. A glutaraldehyde solution is added to the pyridoxylated hemoglobin solution at a molar ratio of glutaraldehyde to hemoglobin of about 24:1. The glutaraldehyde solution is typically added over a period of about 2.5 hours by metering pump to the hemoglobin solution. The polymerization reaction is allowed to proceed for about 15-18 hours. The target molecular weight distribution is about 75% polymer and 25% tetramer. The target polymers have molecular weights of less than about 600 KDa with a predominant fraction of the molecular weights residing in the 100 KDa-350 KDa range.

When the polymerization reaction reaches the target molecular weight distribution (after about 15-18 hours), aqueous glycine is added (as a quench) to the hemoglobin solution at a 140:1 molar ratio of glycine to hemoglobin. The solution pH at this point is 8.9. The resulting solution is then mixed for about 30-40 minutes after which a sodium borohydride sodium/hydroxide solution (having the concentration identified above) is added to the hemoglobin solution at a 28:1 molar ratio of sodium borohydride to hemoglobin. This resulting mixture is stirred for about 1 hour. The solution is then concentrated by ultrafiltration and washed with 4 volumes of WFI. An additional aliquot of sodium borohydride at the same molar ratio as indicated above is added to the concentrated solution and again mixed for 1 hour. The resulting solution is washed with 4 volumes of WFI resulting in polymeric, pyridoxylated, stroma-free hemoglobin that has been heat treated.

The resulting solution is oxygenated by allowing the solution to stand under an oxygen atmosphere. The hemoglobin is then diluted to about 4% total hemoglobin. The 4% total hemoglobin solution is then diafiltered using 10 mM NaCl/20 mM NaOH and a 300 KDa ultra-filter. The filtration is continued until about 97% of the hemoglobin material passes through the filter and is continuously concentrated to 4-8% total hemoglobin using a 70 KDa ultrafilter. (About 3% of the material, i.e., high molecular weight polymers is retained).

The resulting material is about 4-8% total hemoglobin and contains about 25% tetramer. Subsequently, the polymeric hemoglobin-containing material may then be subjected to the heat treatment as discussed in Example 1 to remove dimer and unmodified Hb tetramer.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes exemplary embodiments of the invention, these descriptions should not be viewed in a limiting sense. Rather, variations and modifications may be made without departing from the scope of the present invention as defined in the appended claims.

The invention claimed is:

1. A method for the preparation of an oxygen carrier-containing pharmaceutical composition, the oxygen carrier-containing pharmaceutical composition including hemoglobin, the hemoglobin including cross-linked polymeric hemoglobin, the method comprising:
   (a) providing whole blood including at least red blood cells and plasma;
   (b) separating the red blood cells from the plasma in the whole blood;
   (c) filtering the red blood cells that were separated from the plasma to obtain a filtered red blood cell fraction;
   (d) lysing the red blood cells to create a solution comprising a lysate of disrupted red blood cells;
   (e) extracting a first hemoglobin solution from the lysate;
   (f) performing one or more purification processes on the first hemoglobin solution;
   (g) cross-linking hemoglobin tetramers in the first hemoglobin solution to create a second hemoglobin solution including cross-linked polymeric hemoglobin, the polymeric hemoglobin including two or more cross-linked hemoglobin tetramers;
   (h) heat treating the second hemoglobin solution including the cross-linked polymeric hemoglobin in a deoxygenated environment at a temperature greater than 85° C. and less than or equal to approximately 95° C. for a period of less than approximately 40 minutes to denature and precipitate any residual non-reacted hemoglobin, non-stabilized hemoglobin (dimer) and any other impurities;
   (i) cooling the heat-treated solution to a temperature approximately less than or equal to 25° C. in approximately two minutes or less to prevent formation of met-hemoglobin;
   (j) removing precipitate by a centrifugation or a filtration apparatus to form a solution of hemoglobin including cross-linked polymeric hemoglobin.

2. The method of claim 1 further comprising adding N-acetyl cysteine immediately following heat treating.

3. The method of claim 1 wherein the cooling is performed in less than one minute.

4. The method of claim 1 wherein the heat treatment occurs at a temperature range of greater than 85° C. and less than 90° C. for a period from about 8 minutes to about 30 minutes.

5. The method of claim 1 wherein the heat treatment occurs at approximately 90° C. for a period from about 45 seconds to about 150 seconds.

6. The method of claim 1 wherein the heat treatment occurs at approximately 95° C. for a period from 30 to about 100 seconds.

7. The method of claim 1 further comprising adding N-acetyl cysteine immediately prior to heat treating.

8. The method of claim 2 further comprising adding N-acetyl cysteine immediately prior to heat treating.

9. The method of claim 1 wherein the performing one or more purification processes includes ultrafiltration.

10. The method of claim 1 wherein the performing one or more purification processes includes chromatography.

* * * * *